(12) United States Patent
Williams et al.

(10) Patent No.: US 7,094,208 B2
(45) Date of Patent: Aug. 22, 2006

(54) SPIROMETER

(75) Inventors: David R. Williams, Chicago, IL (US); Nicole April Wilson, Lombard, IL (US); Kevin Philip Meade, Westmont, IL (US); Hansen A. Mansy, Justice, IL (US)

(73) Assignee: Illinois Institute of Technology, Chicago, IL (US)

( * ) Notice: Subject to any disclaimer, the term of this patent is extended or adjusted under 35 U.S.C. 154(b) by 0 days.

(21) Appl. No.: 10/115,263

(22) Filed: Apr. 3, 2002

(65) Prior Publication Data

US 2003/0191407 A1 Oct. 9, 2003

(51) Int. Cl.
*A61B 5/08* (2006.01)
(52) U.S. Cl. ...................................... 600/538; 600/538
(58) Field of Classification Search ........ 600/538–542; 73/861.19
See application file for complete search history.

(56) References Cited

U.S. PATENT DOCUMENTS

| | | | |
|---|---|---|---|
| 3,735,752 A | 5/1973 | Rodder | |
| 4,182,172 A * | 1/1980 | Wennberg et al. | ....... 73/861.19 |
| 4,244,230 A | 1/1981 | Bauer | |
| 4,282,883 A * | 8/1981 | Yerushalmy | ................. 600/539 |
| 4,550,614 A | 11/1985 | Herzl | |
| 4,562,867 A | 1/1986 | Stouffer | |
| 4,843,889 A | 7/1989 | Mansy et al. | |
| 5,137,026 A | 8/1992 | Waterson et al. | |
| 5,277,196 A | 1/1994 | Hankinson et al. | |
| H1282 H * | 2/1994 | Joyce et al. | ........... 128/204.23 |
| 5,363,704 A | 11/1994 | Huang | |
| 5,396,808 A | 3/1995 | Huang et al. | |
| 5,396,809 A | 3/1995 | Huang | |
| 5,518,002 A | 5/1996 | Wolf et al. | |
| 5,562,101 A | 10/1996 | Hankinson et al. | |
| 5,642,735 A | 7/1997 | Kolbly | |
| 5,864,067 A | 1/1999 | Ligneul et al. | |
| 6,216,702 B1 | 4/2001 | Gjers.o slashed.e | |
| 6,305,212 B1 * | 10/2001 | Drzewiecki | ................. 73/23.2 |

FOREIGN PATENT DOCUMENTS

| | | |
|---|---|---|
| EP | 178 042 | 4/1986 |
| WO | 89/12423 | 12/1989 |

OTHER PUBLICATIONS

Uzol O, Camci C. Experimental and Computational Visualization and Frequency Measurements of the Jet Oscillation Inside a Fluidic Oscillator, Piv '01 Paper 1029, pp. 1-9, 2001.
American Thoracic Society, Standardization of Spirometry, 1994 Update. Am J Respir Crit Care Med. 1995 152;1107-1136.

(Continued)

*Primary Examiner*—Robert L. Nasser
(74) *Attorney, Agent, or Firm*—Pauley Petersen & Erickson

(57) ABSTRACT

A spirometer for measuring fluid flow, particularly associated with exhalation of respiratory patients. The spirometer of this invention preferably has a fluidic oscillator wherein the fluid oscillates within a chamber of the fluidic oscillator. An oscillation frequency of the fluid flow within the chamber is correlated to a flow rate. A computer is used to process input data, such as data representing frequency of the oscillatory flow within the chamber, to a flow rate passing through the spirometer. The spirometer of this invention may have no moving parts, which results in the need for only a design calibration and no periodic calibrations throughout use of the spirometer.

17 Claims, 7 Drawing Sheets

OTHER PUBLICATIONS

Monma M, Yamaya M, Sekizawa K, et al. Increased carbon monoxide in exhaled air of patients with seasonal allergic rhinitis. Clin Exp Allergy. Nov. 1999; 29(11): 1537-41.

Muranaka H, Higashi E, Itani S, et al. Evaluation of nicotine, cotinine, thiocyanate, carboxyhemoglobin, and expired carbon monoxide as biochemical tobacco smoke uptake parameters. Int Arch Occup Environ Health. 1988; 60(1): 37-41.

Bendtsen P, Hannestad U, Pahlsson P. Evaluation of the carbon 13-labeled Ketoisocaproate breath test to assess mitochondrial dysfunction in patients with high alcohol consumption. Alcohol Clin Exp Res. Nov. 1998; 22(8): 1792-5.

Hrubá D, Zachovalová L, Fiala J, et al. Evaluation of the level of nicotine dependence among adolescent smokers. Cent Eur J Public Health. Sep. 2003; 11(3): 163-8.

* cited by examiner

SPIROMETER

BACKGROUND OF THE INVENTION

1. Field of the Invention

This invention relates to a spirometer, particularly a fluidic oscillator spirometer, for measuring respiratory flow rates.

2. Description of Related Art

In the United States, the American Thoracic Society (ATS) sets guidelines and standards for treatment of people with respiratory disease. ATS guidelines suggest that lung function should be monitored regularly for patients with known respiratory disease. Patients use daily home monitoring of peak flow to periodically check respiratory flow.

Patients and doctors use three main types of conventional devices to assess lung function: standard spirometers, monitoring spirometers, and peak flow meters. Standard spirometers, often used in a medical office, provide the most reliable results. However, standard spirometers are relatively expensive and require significant user training for proper operation. Standard spirometers are not portable and often require the user to own a computer to operate the spirometer.

Standard spirometers produce the most accurate results when assessing lung function. However, the cost of a standard spirometer ranges from about $ US 2,000 to about $ US 10,000, and thus are not readily available or practical for daily home use. Also, standard spirometers can become less accurate as respiratory flow rates become relatively low. Patients with respiratory disease often can achieve only relatively low flow rates during exhalation, and thus the standard spirometer operates in a less accurate range.

The standard spirometer uses a pneumotachigraph, in which fluid flows through hundreds of small tubes and the flow rate is determined by measuring a pressure drop across the tubes. In pneumotach spirometers, air that flows through the tubes is moist and often full of mucus debris. The tubes can become clogged with the mucus debris, which further reduces the accuracy of the standard spirometer. Also, such standard spirometers are difficult to clean and sterilize, primarily because they must be disassembled for thorough cleaning.

Standard spirometers require daily calibration of a pressure drop across the pneumotach. The calibration process is time-consuming and awkward.

Monitoring spirometers are relatively new for pulmonary medicine. The corresponding devices are relatively small and thus portable, and more conducive for home monitoring uses. However, monitoring spirometers are less accurate than standard spirometers. Most monitoring spirometers are used to manually record spirometry values which are typically displayed, for example on a relatively small liquid crystal display. Also, manual recording of spirometry values requires diligent compliance on a daily routine. Because home compliance is a significant problem with daily physical activities at home routines, manually recorded results are often inaccurate and result in an incorrect diagnosis.

Most monitoring spirometers simply report spirometry values. A common measurement in lung function testing is Forced Expiratory Volume in one second ($FEV_{1.0}$), which relates to the volume of air that a patient can forcefully exhale during the first second of exhalation. However, information contained in the $FEV_{1.0}$ value is not as useful to the physician as a graph of the time-volume curve for each day. The time-volume curve can convey to the physician the nature of the disease but in contrast, a simple number value cannot convey such information. Most standard spirometers produce a time-volume curve but most monitoring spirometers do not produce a time-volume curve.

Conventional peak flow meters can be used to assess lung function. Peak flow meters are relatively inexpensive, portable devices that set the current standard for home monitoring. Peak flow meters measure only a maximum flow rate that a patient can achieve during forceful exhalation. The maximum flow rate measurement provides relatively little useful diagnostic information. However, some physicians believe that because diagnostic results obtained using a measure of peak flow rate are not worth the time, effort and expense involved, patients may avoid use of peak flow meters when performing daily tests.

Some pulmonary physicians believe that daily monitoring of lung function is potentially as beneficial to individuals with lung disease as daily monitoring of blood sugar levels is to individuals with diabetes mellitus, particularly if the respiratory monitoring device can provide diagnostically useful information in a reliable form. It is apparent that there is a need for a spirometer that is relatively small, portable, inexpensive and that can accurately measure, process and record respiratory flow rates.

SUMMARY OF THE INVENTION

It is one object of this invention to provide a spirometer that is relatively small and can be used as handheld device, particularly in a home environment.

It is another object of this invention to provide a spirometer that uses a fluidic oscillator to measure respiratory flow rates.

It is another object of this invention to provide a spirometer that measures and records predetermined data that a physician can analyze to diagnose lung function.

It is still another object of this invention to provide a spirometer that has no moving parts and that requires no frequent calibration.

The above and other objects of this invention are accomplished with a spirometer that operates with a fluidic oscillator. The spirometer of this invention measures a range of parameters, including Forced Vital Capacity (FVC), which is the amount of air a person can forcefully exhale and including $FEV_{1.0}$. These particular measurements are significantly more valuable than peak flow measurements, for both diagnostic and monitoring purposes. The spirometer of this invention can electronically record and calculate all measurements. Recordings are stored locally on the device and data can later be transferred to another source, such as a personal computer.

The spirometer of this invention is relatively small and portable, and can be easily and accurately used in a home environment. With the spirometer of this invention, patients can self-monitor between visits to the doctor. The spirometer of this invention eliminates the need for manual recording of respiratory or pulmonary data received as a result of daily monitoring.

BRIEF DESCRIPTION OF THE DRAWINGS

The above and other features of this invention are apparent when this specification is read in view of the drawings, wherein.

DESCRIPTION OF PREFERRED EMBODIMENTS

Figure 1:
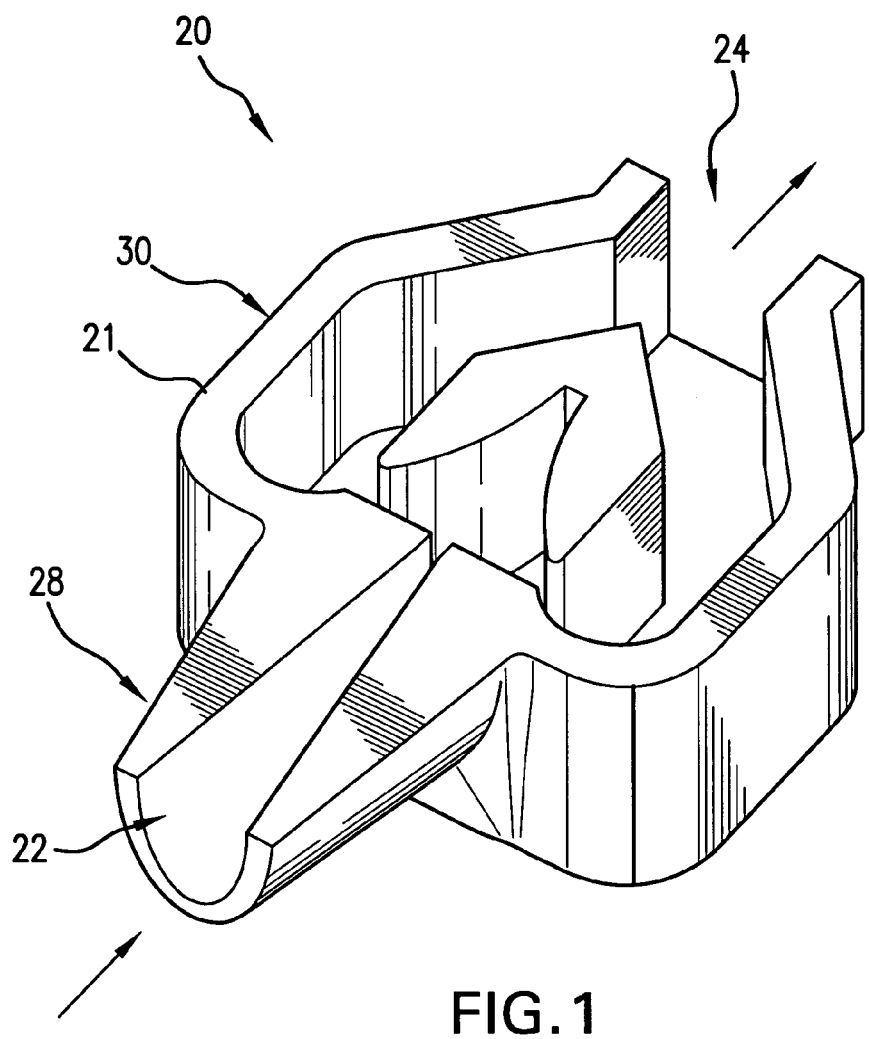
FIG. 1 is a perspective view of one half of an oscillatory flow spirometer, cut along and symmetric about a centerline, according to one embodiment of this invention.
Figure 1A:
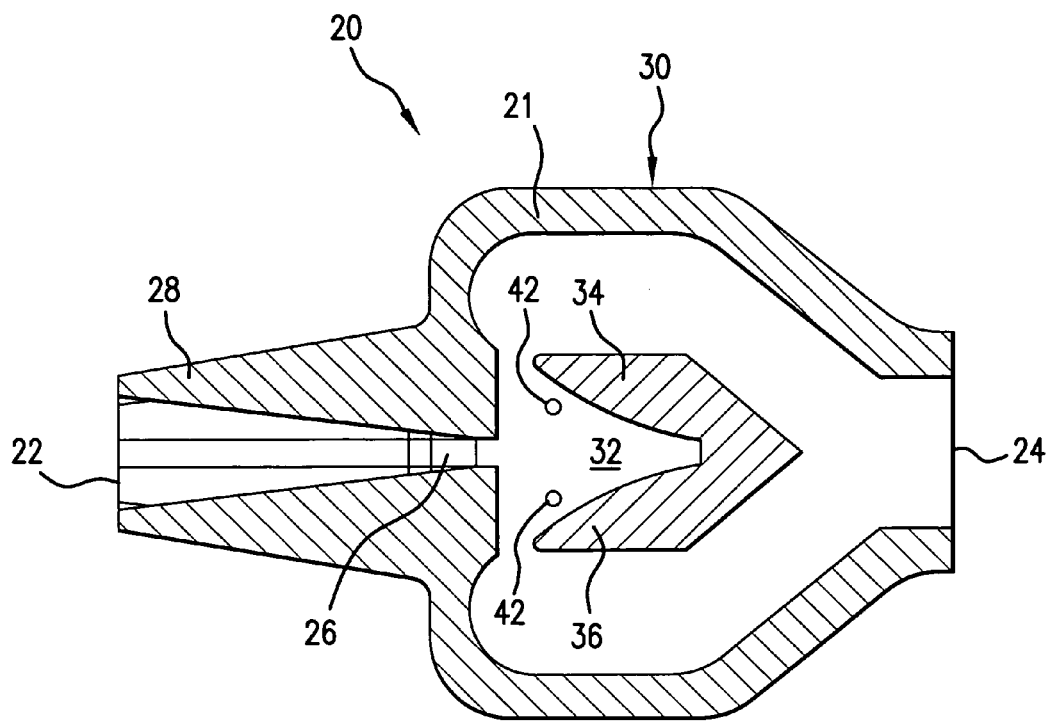
FIG. 1A is a sectional view along a centerline of the oscillatory flow spirometer, as shown in FIG. 1.
Figure 1B:
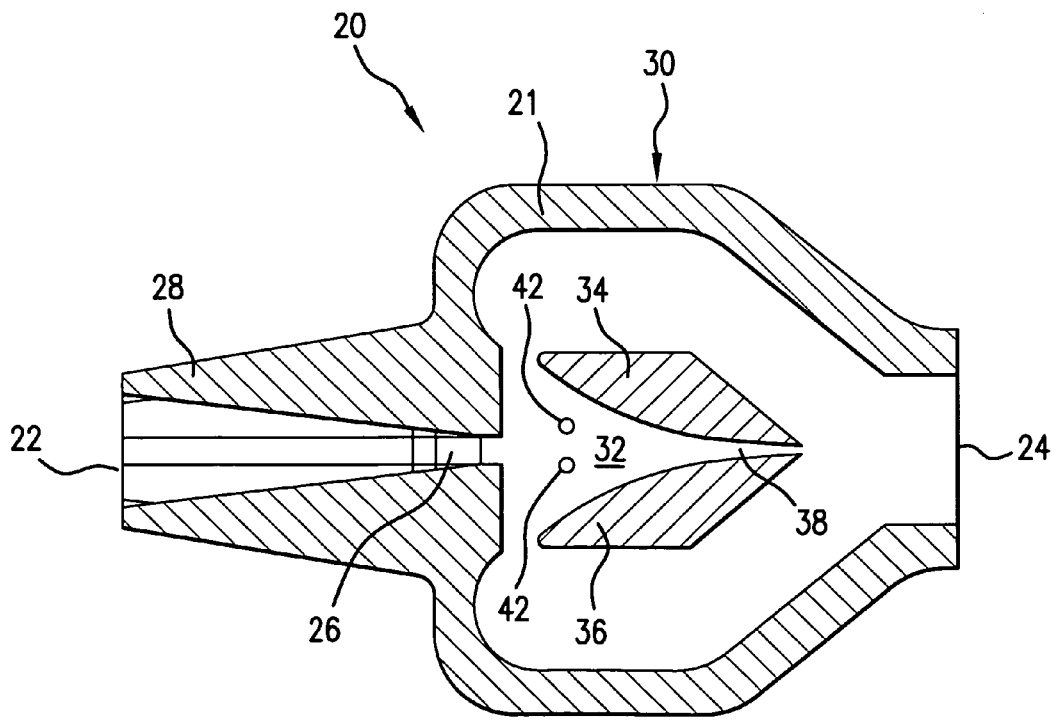
FIG. 1B is a sectional view along a centerline of an oscillatory flow spirometer, similar to the embodiment shown in FIGS. 1 and 1A but having a gap between wedge elements.

Spirometer 20 of this invention is a relatively small, preferably handheld device that operates using principles of oscillatory flow. Throughout this specification and in the claims, the word fluid is intended to relate to air or the fluidic content of an exhalation discharge from a patient, or any other similar fluid. The fluid enters spirometer 20 through inlet 22, and is ultimately discharged through outlet 24, as shown in FIGS. 1, 1A and 1B.

Mouthpiece 28 can be mounted directly or indirectly with respect to nozzle 26, so that the fluid flows through mouthpiece 28, through nozzle 26 and also through inlet 22.

According to one embodiment of this invention, spirometer 20 comprises a fluidic oscillator flowmeter. Conventional fluidic oscillator devices exist. For example, U.S. Pat. Nos. 4,843,889 and 5,363,704, the teachings of which are incorporated into the specification by reference to both United States patents, teach a fluidic oscillator, for example one that can be used as fluidic oscillator 30 of this invention.

Fluidic oscillator 30 of this invention comprises chamber 32. In a used condition of spirometer 20, where fluid flows through spirometer 20, the fluid oscillates within chamber 32. As shown in FIG. 1, wedge elements 34 and 36 are mounted within chamber 32. In one embodiment of this invention, fluid flows into chamber 32 and impinges or otherwise contacts wedge elements 34 and 36. The shape, size and/or position of each wedge element 34, 36 can be varied to accomplish different oscillatory fluid flow parameters.

Depending on the shape of chamber 32 and the particular layout, size and/or shape of each wedge element 34, 36, spirometer 20 can be calibrated as a function of predetermined design. In one embodiment of this invention, fluidic oscillator 30 has no moving parts. In another embodiment of this invention spirometer 20, including all elements, has no moving parts. Without moving parts, spirometer 20 can be accurately calibrated initially and require no later periodic calibration.

Figure 3:
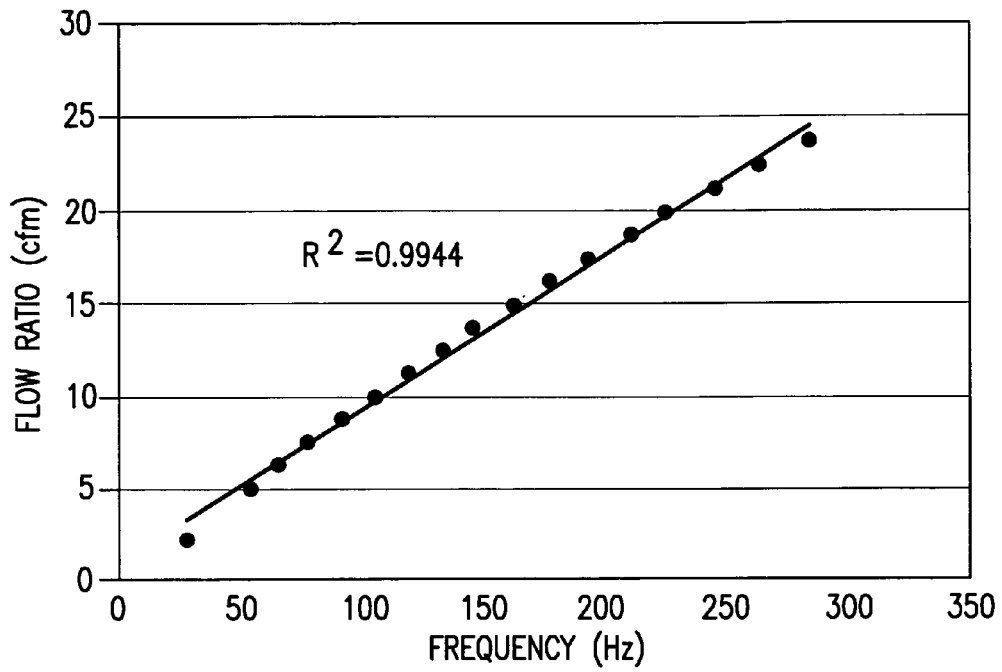
FIG. 3 is a graph showing flow rate versus frequency for a fluidic oscillator, according to one embodiment of this invention.
Figure 4:
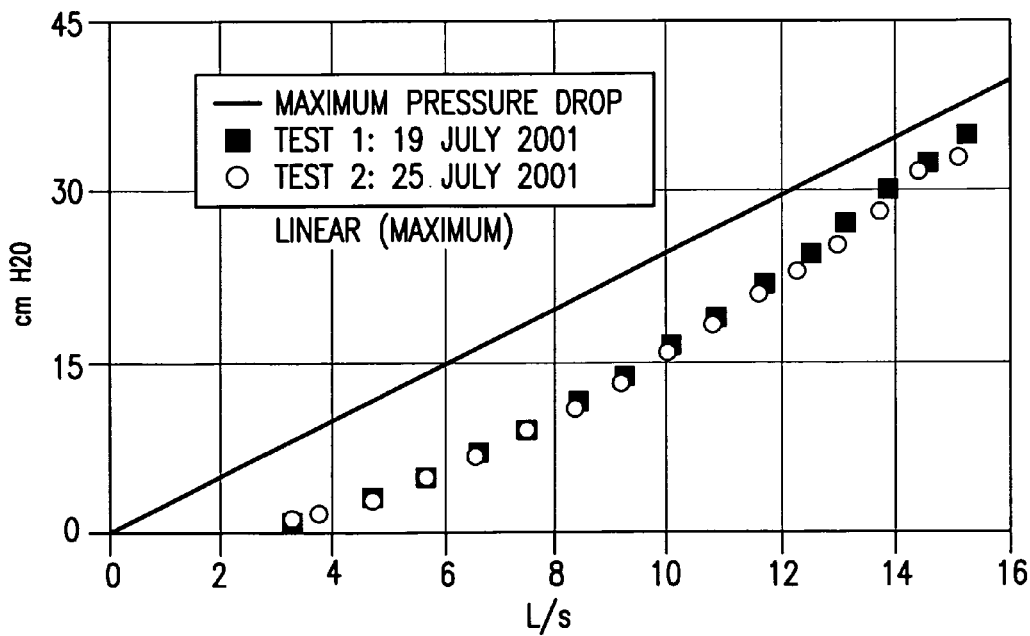
FIG. 4 is a graph of pressure drop versus flow rate, wherein the solid line represents a maximum allowable pressure drop according to the American Thoracic Society Standardization of Spirometry 1994 Update.
Figure 5:
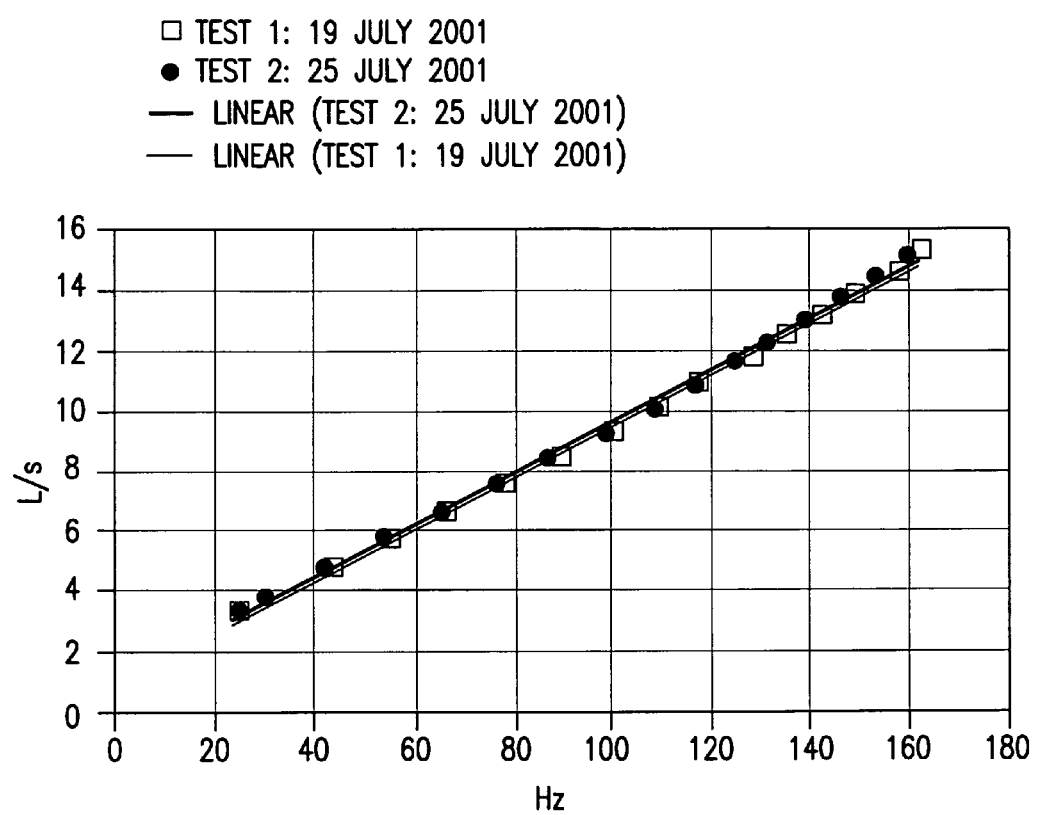
FIG. 5 is a graph illustrating a linear frequency response of a fluidic oscillator, according to one preferred embodiment of this invention.

In one embodiment of this invention, oscillation frequency in chamber 32 is linearly proportional to the flow rate of the fluid entering through inlet 22. FIG. 3 shows a graph of oscillation frequency versus flow rate. The frequency of oscillation can be linearly correlated to flow rate. R-squared values can be determined using a least squares regression technique, such as known to those skilled in the art of mathematics.

Figure 2:
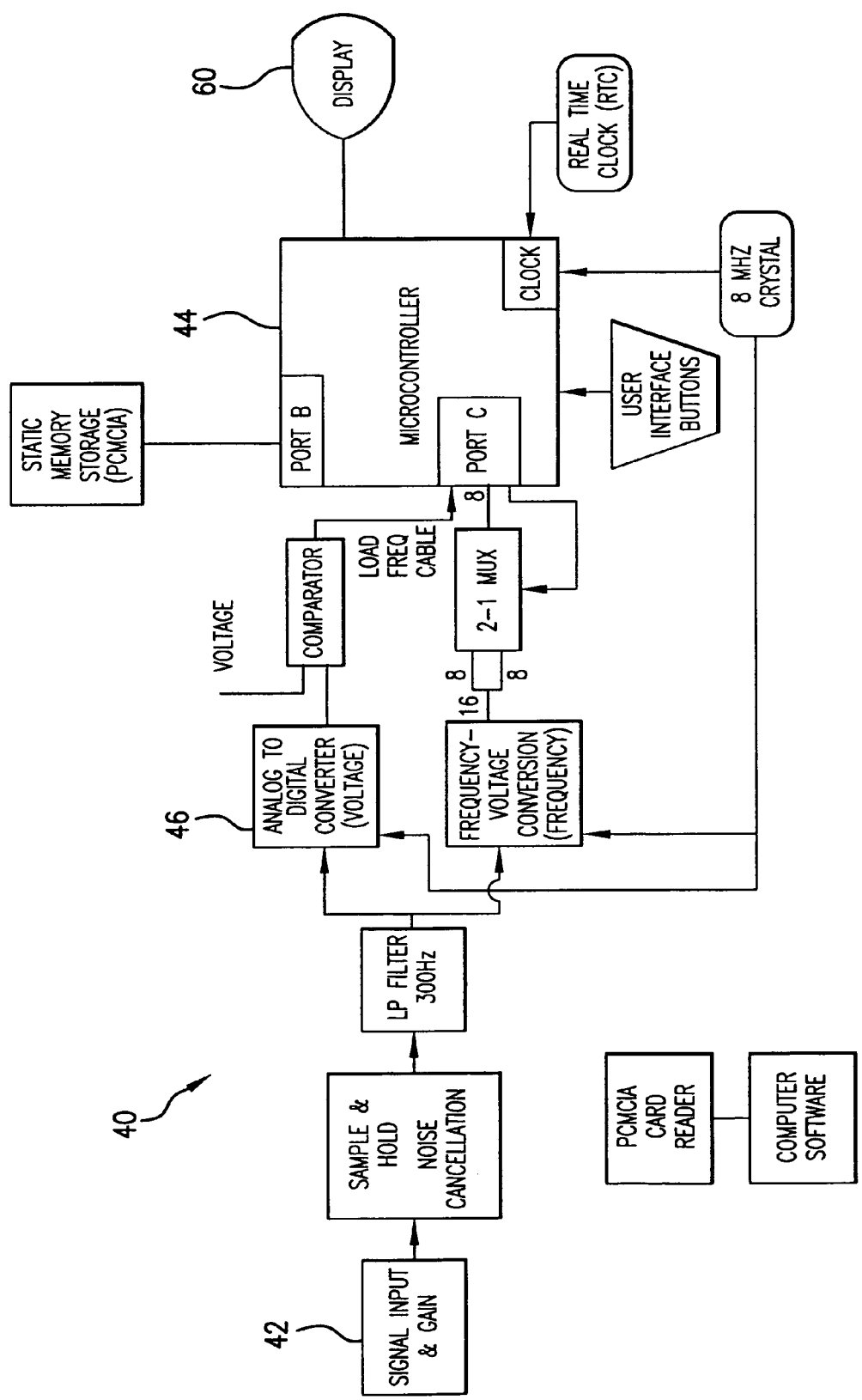
FIG. 2 is an electronics system diagram showing operation of a computer or an electronics package associated with the spirometer of this invention.

In one embodiment of this invention, computer 40, as shown in FIG. 2, is used to measure the oscillatory frequency and then to calculate a standard spirometry value or values and one or more time-volume curves. Computer 40 can comprise any suitable processing device mounted within any suitable frame or other hardware, such as known to those skilled in the art of computers. The hardware can be mounted directly to or with respect to housing 21 of spirometer 20.

A processor of computer 40 can be designed specifically for spirometer 20 of this invention, and can include an analog sensing circuit, with sensor 42, such as an integrated thermistor or pressure transducer, for sensing fluidic oscillations. The processing unit may also comprise a 16-bit analog-to-digital conversion unit with parallel output, a frequency-to-voltage convertor, a microcontroller, and flash memory cards or another suitable digital data storage device.

Sensor 42 detects pressure fluctuations and correlates detected data to an oscillation frequency.

Fluidic oscillation can be varied by selecting a position of wedge elements 34 and 36 with respect to each other. In one preferred embodiment, wedge element 34 contacts wedge element 36. In another embodiment, wedge element 34 is integrated as one piece with wedge element 36. In another embodiment of this invention, such as shown in FIG. 1B, gap 38 is defined between wedge element 34 and wedge element 36, or as disclosed in U.S. Pat. No. 4,843,889.

Sensor 42 can send an input signal, either analog or digital, to the microcontroller of computer 40. The input signal can be transmitted as an analog signal to the microcontroller and then converted to a digital signal or can be converted to a digital signal locally at sensor 42 and then transmitted to the microcontroller.

In one embodiment of this invention, the microcontroller can be programmed or loaded with a suitable algorithium that corresponds to particular data, such as the data as shown in FIG. 3. The microcontroller can then process input data and produce an output signal which can be delivered to output device 60. Output device 60 may comprise any suitable hardware, such as a monitor or other readout display, mounted with respect to housing 21 of spirometer 20.

Computer 40 can provide an interface between frequency and/or flow rate information obtained from chamber 32 and the resultant volumetric flow measurements. In one embodiment of this invention, sensor 42 comprises a thermistor sensing the fluidic oscillations and a processor which calculates and determines the FVC and $FEV_{1.0}$, and can store results as calculated values and/or arithmetic equations.

In one embodiment of this invention, computer 40 calculates and determines the flow rate through spirometer 20 as a function, such as a directly proportional function, of an oscillation frequency of the fluid passing through chamber 32.

In one embodiment of this invention, the oscillation frequency is in a range from about 0 Hz to about 400 Hz, but depending upon the design of chamber 32 the oscillation frequency can be higher. According to one embodiment of this invention, it is only necessary to measure the oscillation frequency to determine the flow rate. Once spirometer 20 of this invention is calibrated for a particular design, it is not necessary to measure pressure drops across any one or more elements of spirometer 20. Sensor 42 produces an output signal which is eventually converted to an electrical signal. The electrical signal is preferably amplified and/or further processed.

Figure 6A:
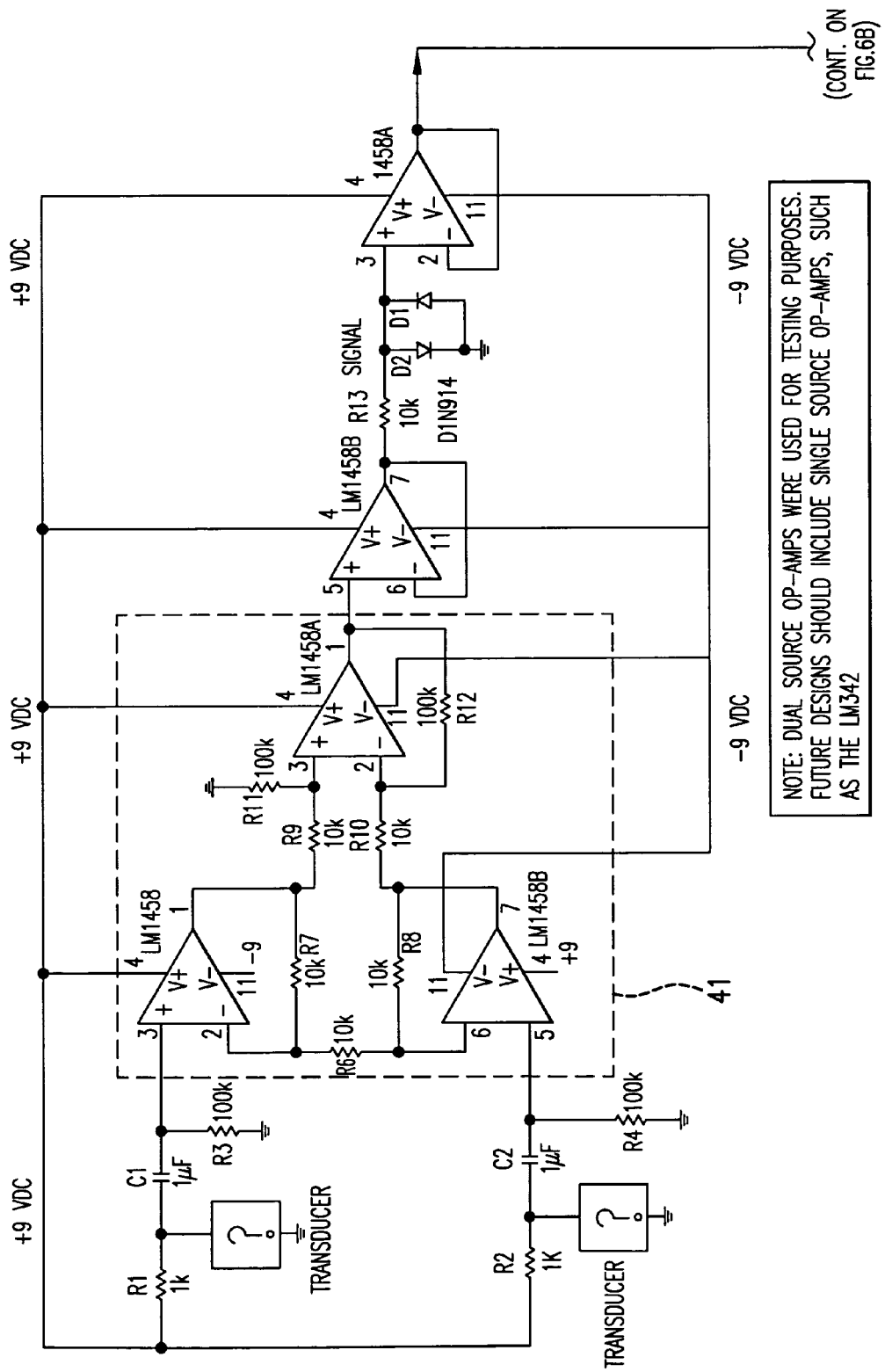
FIG. 6 is a schematic diagram of a differential amplifier and a zero crossing detector, according to one embodiment of this invention.
Figure 6B:
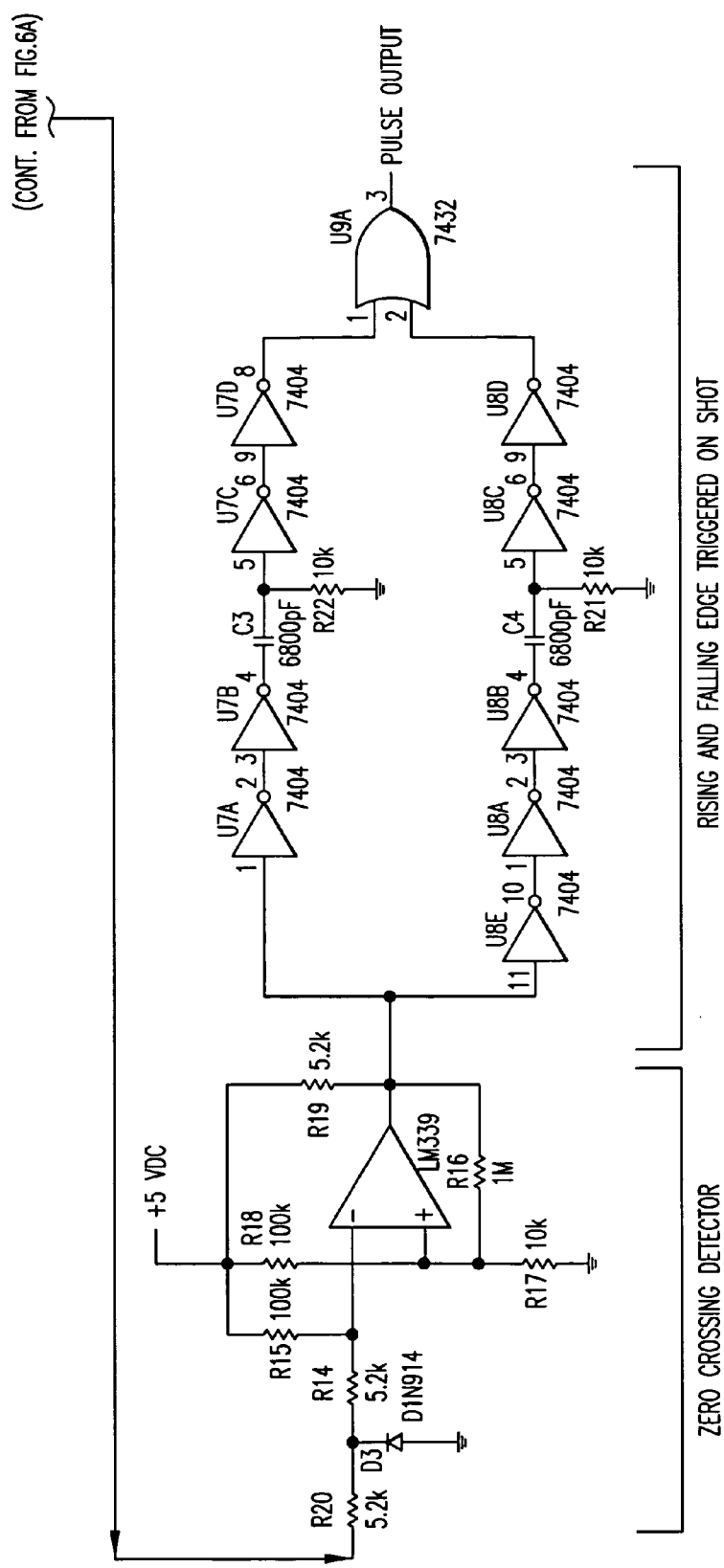

FIG. 6 shows one embodiment of an electrical circuit that can be used as part of computer 40. The dashed lines shown in FIG. 6 identify differential amplifier circuit 41, the type shown and other types of which are known to those skilled in the art of electronic circuits. Many different operational amplifiers, filters and/or buffers can be used to process the output signal emitted by sensor 42.

In one embodiment of this invention, a zero crossing detector, which operates as a function of a voltage magnitude of an electrical signal that alternates between a positive maximum and a negative maximum about a reference voltage, can be used to identify the oscillation frequency. A voltage comparator, such as an operational amplifier device that compares voltages at input terminals, can also be used as part of the zero crossing detector. FIG. 6 shows one embodiment of a zero crossing detector that can be used with computer 40 of this invention.

In one embodiment of this invention, a method for determining an exhalation flow rate of a respiratory system uses spirometer 20 of this invention. Fluid flow is directed into nozzle 26 and passed through inlet 22, into chamber 32 of fluidic oscillator 30. The fluid flow oscillates within chamber 32 and an oscillation frequency of the fluid flow is detected within chamber 32. An input signal representing an oscillation frequency within chamber 32 is detected and delivered to computer 40, which then processes the input signal and emits an output signal. The output signal correlates a flow rate of the fluid flow, which is preferably but not necessarily linearly proportional to the oscillation frequency. In one embodiment of this invention, a least squares regression analysis is used to calibrate, such as initially, spirometer 20 and a resulting linear equation is used to calculate the flow rate as a function of the oscillation frequency. The output signal can be delivered to an output device and displayed for reading purposes, or can be further delivered to another electronic device for further signal processing.

Spirometer 20 of this invention can be used to determine and process volumetric flow data which can be useful in pulmonary medicine. Spirometer 20 of this invention can be designed and calibrated to conform to guidelines set by the American Thoracic Society (ATS). ATS guidelines require a specific pressure drop across the flow meter and spirometer 20 of this invention can be designed to meet any such specific pressure drop requirement.

ATS guidelines may also require the nozzle of a spirometer to have a specific pressure drop. Nozzle 26 of this invention can be designed to meet any such specific pressure drop requirement. Mouthpiece 28 can be attached directly or indirectly to nozzle 26. The design of mouthpiece 28 is selected to structurally conform with and correspond to nozzle 26, and so that particular flow parameters are achieved through mouthpiece 28 and nozzle 26, for entry into inlet 22. Mouthpiece 28 preferably fits comfortably within a patient's mouth.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. An apparatus for determining an entire exhalation flow rate of a respiratory system, the apparatus comprising:
a spirometer having an inlet for accepting the entire exhalation flow rate and having an outlet, a nozzle in communication with the inlet, a fluidic flow oscillator in communication with the inlet and the outlet, and the fluidic flow oscillator passing the entire exhalation flow rate at a maximum pressure drop across the spirometer that is less than 1.5 $cmH_2O$ per L/s between a flow rate of zero and 14 L/s.

2. The spirometer according to claim 1, wherein the fluidic oscillator flowmeter has a chamber, and in a use condition a fluid flow passing through the spirometer oscillates in the chamber.

3. The spirometer according to claim 2, further comprising a computer, a sensor positioned within the chamber, the sensor detecting an oscillation frequency of the fluid flow within the chamber and emitting a corresponding input signal to the computer.

4. The spirometer according to claim 3, wherein the wedge elements are shaped so that the oscillation frequency of the fluid flow in the chamber is linearly proportional to a flow rate of the fluid flow.

5. The spirometer according to claim 3 wherein the sensor comprises an analog sensing circuit that emits the input signal as an analog signal, and the computer comprises a microcontroller and a convertor that receives and converts the analog signal to a digital signal for the microcontroller to process.

6. The spirometer according to claim 5, further comprising an output device displaying a processed signal emitted by the microcontroller, and the output device mounted with respect to a body of the fluidic oscillator flowmeter.

7. The spirometer according to claim 2, wherein the fluidic oscillator flowmeter has two wedge shaped elements positioned opposite each other, and a gap is formed between the wedge elements.

8. The spirometer according to claim 1, further comprising a mouthpiece mounted with respect to a body of the fluidic oscillator flowmeter and in communication with the nozzle.

9. The spirometer according to claim 1, further comprising a mouthpiece in communication with the nozzle.

10. A method for determining an exhalation flow rate of a respiratory system, the method comprising:
discharging an entire exhalation fluid flow into a nozzle of a spirometer, and passing the entire exhalation fluid flow from the nozzle into and through a fluidic oscillator flowmeter at a maximum pressure drop across the spirometer that is less than 1.5 $cmH_2O$ per L/s between a flow rate of zero and 14 L/s.

11. The method according to claim 10, wherein the entire exhalation fluid flow passes from the nozzle through an inlet of the fluidic oscillator flowmeter and into a chamber of the fluidic oscillator flowmeter.

12. The method according to claim 10, wherein the entire exhalation fluid flow oscillates within a chamber of the fluidic oscillator flowmeter.

13. The method according to claim 12, wherein an oscillation frequency of the entire exhalation fluid flow is detected within the chamber.

14. The method according to claim 13, wherein an input signal representing the oscillation frequency is computed into an output signal.

15. The method according to claim 14, wherein the output signal correlates to a flow rate of the entire exhalation fluid flow which is linearly proportional to the oscillation frequency.

16. The method according to claim 15, wherein the flow rate is calculated as a linear function of the oscillation frequency.

17. The method according to claim 14, wherein the output signal is delivered to an output device.

* * * * *